United States Patent [19]

Kagawa et al.

[11] Patent Number: 5,258,521
[45] Date of Patent: Nov. 2, 1993

[54] PROCESS OF PRODUCING OPTICALLY ACTIVE PROPIONIC ACID ESTER DERIVATIVES

[75] Inventors: Takumi Kagawa, Shinnanyo; Mikio Ito, Tokuyama; Syunji Aman, Shinnanyo; Takashi Morooka, Shinnanyo; Hiroyuki Watanabe, Shinnanyo; Kenji Tsuzuki, Shinnanyo, all of Japan

[73] Assignee: Tosoh Corporation, Yamaguchi, Japan

[21] Appl. No.: 556,716

[22] Filed: Jul. 25, 1990

[30] Foreign Application Priority Data

Jul. 26, 1989 [JP] Japan .................. 1-191252
Sep. 11, 1989 [JP] Japan .................. 1-232861
Sep. 18, 1989 [JP] Japan .................. 1-240266
Oct. 13, 1989 [JP] Japan .................. 1-264984
Oct. 31, 1989 [JP] Japan .................. 1-281805
Nov. 15, 1989 [JP] Japan .................. 1-294805
Dec. 14, 1989 [JP] Japan .................. 1-322574

[51] Int. Cl.$^5$ .................. C07D 213/55; C07D 213/79; A01N 43/40
[52] U.S. Cl. .................. 546/302; 544/354; 546/268; 546/283; 548/170; 549/501
[58] Field of Search .................. 546/268, 283, 302; 544/354; 548/170; 549/501

[56] References Cited

U.S. PATENT DOCUMENTS 3,773,773 11/1973 Bossert .................. 546/268
4,532,328 7/1985 Kleschick .................. 546/302

FOREIGN PATENT DOCUMENTS 0002800 7/1979 European Pat. Off. .......... 546/260
0151429 8/1985 European Pat. Off. .......... 546/302
0248968 6/1986 European Pat. Off. .......... 546/268
0288275 10/1988 European Pat. Off. .......... 546/268
0323727 7/1989 European Pat. Off. .......... 544/354
2348908 11/1977 France .................. 546/260
2412532 7/1979 France .................. 546/268

OTHER PUBLICATIONS

Gilman, et al., Organic Synthesis, 2nd Ed., John Wiley & Sons, New York, pp. 296-299, pp. 434-437 (1972).
Hoening, et al., Organic Synthesis, Collective vol. 3, John Wiley & Sons, New York, pp. 46-49 & 140-141, 146-149, 200-205, 418-421, (1965).
Baumgarten et al., Organic Synthesis, Collective vol. 5, John Wiley and Sons, New York, pp. 250-255, (1960).
Pine, et al., Organic Chemistry, 4th Ed., McGraw-Hill, London, pp. 272-275, 376-379, (1957).
Morrison & Boyd, Organic Chemistry, 5th Edition, Allyn & Bacon, Inc., Boston, 1987, pp. 703, 875, 830.

Primary Examiner—Floyd D. Higel
Attorney, Agent, or Firm—Nixon & Vanderhye

[57] ABSTRACT

Processes for producing optically active ester derivatives are disclosed. According to the present invention an optically active aryloxyphenoxy propionate derivative is produced by reacting a chlorinated heterocyclic aromatic compound with (2R)-2-(4-hydroxyphenoxy)-propionic acid tetrahydrofurfuryl ester in an anhydrous solvent in the presence of a base. According to the present invention, an optically active propionate derivative of the formula [I]

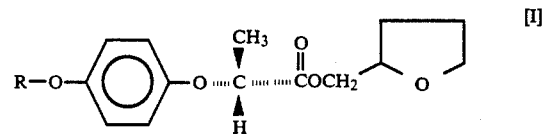

(wherein R represents hydrogen or 3-chloro-5-trifluoromethyl-2-pyridyl group) is produced by reacting a corresponding optically active methyl propionate derivative with tetrahydrofurfuryl alcohol, or by reacting a corresponding optically active propionic acid derivative with tetrahydrofurfuryl alcohol, or by reacting (2S)-tetrahydrofurfuryl 2-chloropropionate with a corresponding phenol derivative in specific conditions.

1 Claim, No Drawings

PROCESS OF PRODUCING OPTICALLY ACTIVE PROPIONIC ACID ESTER DERIVATIVES

BACKGROUND OF THE INVENTION

I. Field of the Invention

This invention relates to a process of producing optically active propionate derivatives. The optically active propionate derivatives are useful as herbicides or intermediates of herbicides.

II. Description of the Related Art

A process of producing racemic 2-(4'-(3''-chloro-5''-trifluoromethyl-2''-pyridyloxy)phenoxy)propionic acid is known and is disclosed in Japanese Laid Open Patent Application (Kokai) No. 119476/79). In this process, 4-(3'-chloro-5'-trifluoromethyl-2'-pyridyloxy)phenol and sodium hydroxide are mixed in toluene at 60° C., then 2-chloropropionic acid is added to the mixture at 50°-80° C. and then the resulting mixture is allowed to react at 110° C. for 1-1.5 hours.

However, if this process is applied to the production of optically active (2R)-2-(4''-(3''-chloro-5''-trifluoro-2''-pyridyloxy)phenoxy)propionic acid, the yield is only 67% and the optical purity of the product is as small as 56%. Further, since (2S)-2-chloropropionic acid used as a starting material is relatively unstable, this material should be prepared immediately before use by hydrolyzing (2S)-2-chloropropionic acid methyl ester which is industrially available, so that the operation is troublesome.

On the other hand, a process of producing optically active (2R)-2-(4'-(3''-chloro-5''-trifluoromethyl-2''-pyridyloxy)phenoxy)propionic acid is known and disclosed in, for example, U.S. Pat. No. 4,532,328. In this process, methanesulfonate of (2S)-lactic acid and 4-(3'-chloro-5'-trifluromethyl-2'-pyridyloxy)phenol are reacted in N,N-dimethylsulfoxide in the presence of potassium carbonate at room temperature for 42 hours. However, with this process, only a product with an optical purity of as low as 66% e.e. can be obtained.

A process of producing propionate derivatives is also known and is disclosed in Japanese Laid Open Patent Application (Kokai) No. 116986/88. In this process, methyl (2S)-2-chloropropionate, hydroquinone and 4-(3'-chloro-5'-trifluoromethyl-2'-pyridyloxy)phenol are used as starting materials and an optically active propionate derivative is prepared therefrom through several steps. Then the obtained optically active propionate derivative is converted to an acid chloride with thionyl chloride, and the acid chloride is reacted with tetrahydrofurfuryl alcohol to obtain the desired product.

However, with this process, since the desired product is obtained after forming optically active (2R)-2-(4'-(3''-chloro-5''-trifluoromethyl-2''-pyridyloxy)phenoxy)propionic acid, two steps are required for obtaining the desired product. Further, since the thionyl chloride used in this process has a tendency to vigorously react with water to decompose, the handling of the substance is troublesome in the industrial scale.

Thus, a process of producing optically active propionate derivative which is simple in operation and by which the desired product with high optical purity may be obtained is needed.

SUMMARY OF THE INVENTION

Accordingly, an object of the present invention is to provide a process of producing optically active propionate derivatives which is simple in operation and by which the desired product with high optical purity may be obtained.

The present inventors intensively studied to develop novel processes of producing optically active propionate derivatives which may be carried out simply and by which the desired products with high optical purity may be obtained.

That is, the present invention provides a process of producing an optically active aryloxyphenoxy propionic acid ester derivative comprising reacting a chlorinated heterocyclic aromatic compound with tetrahydrofurfuryl (2R)-2-(4-hydroxyphenoxy)propionate in an anhydrous solvent in the presence of a base.

The present invention also provides a process of producing an optically active propionic acid ester derivative of the formula [I]

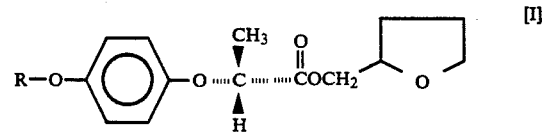

(wherein R represents hydrogen or 3-chloro-5-trifluoromethyl-2-pyridyl group) comprising reacting an optically active methyl propionate derivative of the formula [II]

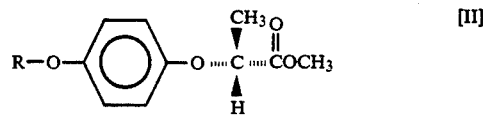

(wherein R represents the same meaning as in formula [I]) with tetrahydrofurfuryl alcohol in the presence of an acid catalyst.

The present invention still further provides a process of producing a propionate derivative of the above-described formula [I] comprising reacting an optically active (2R)-propionic acid derivative of the formula

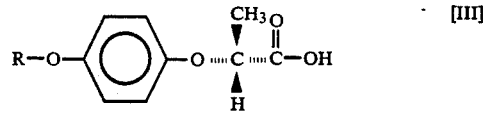

(wherein R represents the same meaning as in formula [I]) with tetrahydrofurfuryl alcohol in the presence of a hydrogen halide.

The present invention further provides a process of producing the propionic acid ester derivative of the above-described formula [I], comprising reacting (2S)-tetrahydrofurfuryl 2-chloropropionate of the formula [IV]

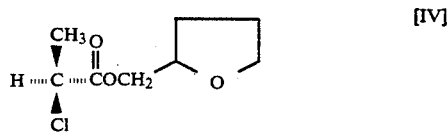

with a phenol derivative of the formula [V]

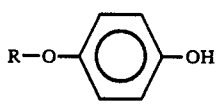

[V]

(wherein R represents the same meaning as in formula [III]) in the presence of a dehydrohalogenating reagent.

The present invention still further provides a process of producing (2R)-2-(4'-(3''-chloro-5''-trifluoromethyl-2''-pyridyloxy)phenoxy)propionic acid comprising the steps of refluxing a solution of 4-(3'-chloro-5'-trifluoromethyl-2'-pyridyloxy)phenol in an aromatic hydrocarbon solvent ar a temperature of not lower than 40° C. and lower than 80° C. under reduced pressure; and adding thereto an aqueous solution containing (2S)-2-chloropropionic acid and a dehydrohalogenating reagent while continuing the reflux so as to dehydrate the resulting mixture concurrently with the addition of said aqueous solution, thereby carrying out the reaction.

The present invention still further provides a process of producing (2R)-2-(4'-(3''-chloro-5''-trifluoromethyl-2''-pyridyloxy)phenoxy)propionic acid comprising the steps of refluxing a solution containing methyl (2S)-2-chloropropionate and 4-(3'-chloro-5'-trifluoromethyl-2'-pyridyloxy)phenol) in an aromatic hydrocarbon solvent at a temperature of not lower than 40° C. and lower than 80° C. under reduced pressure; and adding thereto an aqueous solution of a dehydrohalogenating reagent while continuing the reflux so as to dehydrate the resulting mixture concurrently with the addition of said aqueous solution, thereby carrying out the reaction.

The present invention still further provides a process of producing (2R)-2-(4'-(3''-chloro-5''-trifluoromethyl-2''-pyridyloxy)phenoxy)propionate derivative comprising the steps of refluxing a solution of 4-(3'-chloro-5'-trifluoromethyl-2'-pyridyloxy)phenol in an aromatic hydrocarbon solvent at a temperature of not lower than 40° C. and lower than 80° C. under reduced pressure; adding thereto an aqueous solution containing (2S)-2-chloropropionic acid and a dehydrohalogenating reagent while continuing the reflux so as to dehydrate the resulting mixture concurrently with the addition of said aqueous solution, thereby carrying out the reaction; and adding to the resulting mixture a hydrogen halide and tetrahydrofurfuryl alcohol.

By the present invention, novel industrial processes for producing optically active propionic acid derivatives, by which the optically active propionic acid derivatives with high optical purity may be produced with a high yield were provided. Thus, the present invention will greatly contribute to the herbicide industry.

DETAILED DESCRIPTION OF THE PREFERRED EMBODIMENTS

In the process according to a first aspect of the present invention, aryloxyphenoxypropionic acid esters are prepared by reacting a chlorinated heterocyclic aromatic compound with (2R)-2-(4-hydroxyphenoxy)propionic acid tetrahydrofurfuryl ester (hereinafter also referred to as "propionic acid ester A" for short) in the presence of a base in a non-aqueous solvent.

Preferred examples of the chlorinated heterocyclic aromatic compound may include pyridine compounds such as 2-chloro-5-trifluoromethylpyridine, 2,3-dichloro-5-trifluoromethylpyridine and 2,3,5-trichloropyridine; and condensed heteroaromatic compounds such as 2,6-dichloroquinoxaline, 2,6-dichlorobenzoxazol and 2,6-dichlorobenzothiazol.

Although the heterocyclic compound may be used in the amount of 1-5 moles with respect to 1 mole of propionic acid ester A, since the yield of the desired product is not proved even if more than 1.5 moles of the heterocyclic compound is used with respect to 1 mole of propionic acid ester A, the preferred amount of the heterocyclic compound is 1-1.5 moles per 1 mole of propionic acid ester A.

Preferred examples of the anhydrous aprotic solvent may include aliphatic hydrocarbons such as hexane and pentane; aromatic hydrocarbons such as benzene, toluene and xylene; ethers such as ethyl ether, tetrahydrofuran, monoglyme and diglyme; anhydrous aprotic polar solvents such as dimethylsulfoxide, dimethylformamide and acetonitrile.

The amount of the solvent used may preferably be 1-100 parts by volume with respect to one part by volume of propionic acid ester A.

Preferred examples of the base used in the process may include alkaline metal hydroxides such as lithium hydroxide, sodium hydroxide and potassium hydroxide; carbonates such as sodium carbonate, potassium carbonate, sodium hydrogen carbonate and potassium hydrogen carbonate; and alkaline metal hydrides such as lithium hydride, sodium hydride and calcium hydride.

The amount of the base used is not restricted as long as it is not less than the stoichiometric amount with respect to propionic acid ester A, that is, not less than one mole per one mole of propionic acid ester A. The reaction well proceeds if the amount of the base is 1 to 5 moles per one mole of propionic acid ester A.

The reaction may be carried out preferably under an inert gas such as nitrogen at 0°-150° C., more preferably 30°-120° C., for several minutes to 48 hours.

In the process according to a second aspect of the present invention, the optically active propionic acid ester derivative represented by the above-described formula [I] is prepared by the trans-esterification between the optically active methyl propionate derivative of the above-described formula [II] and tetrahydrofurfuryl alcohol in the presence of an acid catalyst.

The optically active methyl propionate derivative which is a starting material in this process may be obtained easily by reacting methyl (2S)-2-chloropropionate which is industrially available, hydroquinone and 4-(3'-chloro-5'-trifluoromethyl-2'-pyridyloxy)phenol, in the presence of a dehydrohalogenating reagent in the anhydrous condition.

The amount of the tetrahydrofurfuryl alcohol used in this process is not restricted as long as it is not less than one mole with respect to one mole of the optically active methyl propionate derivative. However, if the amount is too small, it takes a long time to complete the reaction and if it is too excess, the process is not economical. Thus, from the practical viewpoint, the amount of the tetrahydrofurfuryl alcohol may preferably be 2 to 40 moles, more preferably 2 to 20 moles per one mole of the optically active methyl propionate derivative.

Preferred examples of the acid catalyst which may be employed in this process may include mineral acids such as sulfuric acid and hydrochloric acid; organic sulfonic acids such as methanesulfonic acid, benzenesulfonic acid and p-toluenesulfonic acid; and trifluoroacetic acid.

Although the amount of the acid catalyst is not restricted, it is preferably 0.01 mol % to 10 mol %, more preferably 0.02 to 5 mol % with respect to the optically active propionic acid methyl ester derivative.

The solvent which is employed in the process may be any solvent which is inactive to the reaction. Examples of the solvent include aromatic hydrocarbons such as benzene, toluene, ethylbenzene and xylene; halogenated hydrocarbon solvents such as dichloromethane, chloroform, carbon tetrachloride and dichloroethane. The tetrahydrofurfuryl alcohol per se may also be used as a solvent.

Although the amount of the solvent is not restricted, it is preferably 10 to 100 parts by weight, more preferably 10 to 50 parts by weight with respect to one part by weight of the optically active methyl propionate derivative. In the case where tetrahydrofurfuryl alcohol is used as the solvent, the amount of the alcohol may preferably be 10–40 moles with respect to one mole of the propionic acid methyl ester derivative.

The process may be carried out at a temperature of 40°–150° C., more preferably 50° to 130° C. at a temperature not higher than the boiling point of the solvent.

Although the time required for completing the reaction varies depending on the reaction temperature, the optically active propionic acid methyl ester derivative employed, and on ratio of the starting reaction components, the reaction usually completes in 50 hours.

After completion of the reaction, excess tetrahydrofurfuryl alcohol is recovered, and the reaction product is extracted with an organic solvent such as toluene and xylene, washed with water and condensed so as to obtain the desired product of the above-described formula [I].

According to a third aspect of the present invention, a process for producing the propionic acid ester derivative represented by the above-described formula [I] is provided in which the (2R)-propionic acid derivative of the above-described formula [III] is reacted with tetrahydrofurfuryl alcohol in the presence of a hydrogen halide.

The (2R)-2-(4'-hydroxyphenoxy)propionic acid which is one of the compound represented by the formula [III] may be prepared by hydrolyzing industrially available (2S)-methyl-2-chloropropionate and then reacting the resultant with hydroquinone. The (2R)-2-(4'-(3"-chloro-5"-trifluoromethyl-2"-pyridyloxy)phenoxy)-propionic acid which is another compound represented by the formula [III] may be obtained by reacting the thus obtained (2R)-2-(4'-hydroxyphenoxy)propionic acid and 2,3-dichloro-5-trifluoromethylpyridine.

Preferred examples of the hydrogen halide used in this process may include hydrogen fluoride, hydrogen chloride, hydrogen bromide and hydrogen iodide. Among these, in view of the reactivity and ease of handling, hydrogen chloride and hydrogen bromide are preferred.

Although the amount of the hydrogen halide is not restricted, if it is too excess, the reaction operation may be troublesome and if it is too small, it takes a long time to complete the reaction. Thus, the amount of the hydrogen halide may preferably be 0.01–0.20 part by weight with respect to one part by weight of tetrahydrofurfuryl alcohol.

Although the amount of tetrahydrofurfuryl alcohol is not restricted as long as it is not less than the stoichiometric amount, i.e., one mole per one mole of optically active propionic acid derivative of the formula [III], if it is too small, it takes a long time to complete the reaction and if it is too excess, the process is not economical. Thus, from the practical point of view, the amount of tetrahydrofurfuryl alcohol may preferably be 5–100 moles per one mole of the propionic acid derivative of the formula [III].

Any solvent which is inactive to the reaction may be employed as the solvent in the process. Preferred examples of the solvent include aromatic hydrocarbons such as benzene, toluene, ethylbenzene, xylene and mesitylene; and halogenated hydrocarbons such as dichloromethane, chloroform and carbon tetrachloride. Further, tetrahydrofurfuryl alcohol per se may also be used as the solvent.

Although the amount of the solvent is not restricted, if it is too small, the optically active propionic acid derivative of the formula [III] may be precipitated in a large amount because the solubility of this substance in organic solvents are small. On the other hand, use of too large amount of solvent is not economical. Thus, the solvent may preferably be used in the amount of 3–30 parts by weight per one part by weight of the propionic acid derivative of the formula [III].

The reaction may be carried out at a temperature of 5°–150° C. which is not higher than the boiling point of the solvent employed. Since the reaction rate of this reaction is larger than the other esterification reactions, the reaction may be well carried out usually at a temperature of 5°–80° C.

Although the time required for completing the reaction varies depending on the mixing ratio of the starting reaction components and on the reaction temperature, usually 0.5 to 8 hours is sufficient for completing the reaction.

By distilling the reaction mixture so as to remove the solvent, hydrogen halide and excess tetrahydrofurfuryl alcohol, the optically active propionate derivative of the formula [III] may be obtained.

According to a fourth aspect of the present invention, a process for producing the optically active propionic acid ester derivative of the formula [I] is provided in which tetrahydrofurfuryl (2S)-2-chloropropionate represented by the above-described formula [IV] is reacted with a phenol derivative represented by the above-described formula [V] in the presence of a dehydrohalogenating reagent.

The optically active tetrahydrofurfuryl (2S)-2-chloropropionate which is used as a starting material in this process may be obtained by treating tetrahydrofurfuryl (2R)-lactate with thionyl chloride so as to change the hydroxide group to chlorine atom, which tetrahydrofurfuryl (2R)-lactate is obtained by esterification reaction between industrially available (2R)-lactic acid and tetrahydrofurfuryl alcohol.

Although the amount of tetrahydrofurfuryl (2S)-2-chloropropionate used in this process is not restricted as long as it is about not less than 1.1 mole per 1 mole of the phenol derivative employed in the reaction, if it is too small, the optical purity of the product may be degraded and if it is too excess, the process is not economical. Thus, tetrahydrofurfuryl (2S)-2-chloropropionate may preferably be used in the amount of 2–20 moles per 1 mole of the phenol derivative.

Examples of the dehydrohalogenating reagents include sodium carbonate, potassium carbonate, sodium hydrogen carbonate and potassium hydrogen carbonate. Among these, sodium carbonate and potassium carbonate are preferred.

Although the amount of the dehydrohalogenating reagent is not restricted as long as it is not less than about 1.1 equivalent with respect to the phenol derivative, since the use of the dehydrohalogenating reagent in large excess is not economical, it is preferably 1.1–10 equivalents.

Any solvent in which the phenol derivative to be used can be dissolved may be employed as a solvent in the process. In view of the reaction rate and the solubility of the starting materials, ketones such as acetone, methylethyl ketone; polar aprotic solvents such as N,N-dimethylformamide, N,N-dimethylsulfoxide and N-methylpyrrolidone are preferred as the solvent.

Although the amount of the solvent is not restricted, if it is too small, the stirring of the mixture may be difficult, and if it is too excess, the process is not economical. Thus, the solvent may preferably be used in the amount of 5–30 parts by weight per one part by weight of the phenol derivative.

Although the reaction temperature appropriate for carrying out the reaction varies depending on the phenol derivative, dehydrohalogenating reagent and the solvent employed, the reaction may usually be carried out at a temperature of 0°–100° C.

The reaction usually completes with 48 hours.

The desired optically active propionate derivative may be obtained by removing the solvent, washing the residue with water, extracting the residue with an organic solvent such as ether and ethylacetate, condensing the extract and further purifying the extract with known method.

According to a fifth aspect of the present invention, a process for producing optically active (2R)-2-(4'-(3''-chloro-5''-trifluoromethyl-2''-pyridyloxy) phenoxy)-propionic acid is provided, in which 4-(3'-chloro-5'-trifluoromethyl-2'-pyridyloxy)phenol (hereinafter also referred to as "PyPOH" for short) is reacted with (2S)-2-chloropropionic acid or methyl (2S)-2-chloropropionate in the presence of a dehydrohalogenating hydrocarbon reagent.

PyPOH which is used in this process may be easily prepared by reacting 2,3-dichloro-5-trifluoromethylpyridine and hydroquinone in the presence of a dehydrohalogenating reagent. The (2S)-2-chloropropionic acid which is another starting material may be quantitatively prepared in a short period of time by reacting industrially available (2S)-2-chloropropionic acid methyl ester and an aqueous solution of a dehydrohalogenating reagent at room temperature. The resulting aqueous solution containing (2S)-2-chloropropionic acid and the dehydrohalogenating reagent may be used as it is in this process or may be used after distilling off the methanol generated as a byproduct under reduced pressure.

In cases where (2S)-2-chloropropionic acid is used, a solution of PyPOH in an aromatic hydrocarbon solvent is refluxed under reduced pressure at a temperature of not lower than 40° C. and lower than 80° C. and then the aqueous solution containing (2S)-2-chloropropionic acid and the dehydrohalogenating reagent is added thereto while keeping the reflux condition so as to dehydrate the resulting mixture concurrently with the addition of the aqueous solution, thereby carrying out the reaction. In cases where methyl (2S)-2-chloropropionate is used, a solution containing methyl (2S)-2-chloropropionate and PyPOH in an aromatic hydrocarbon solvent is refluxed under reduced pressure at a temperature of not lower than 40° C. and lower than 80° C. and then an aqueous solution containing the dehydrohalogenating reagent is added thereto while continuing the reflux so as to dehydrate the resulting mixture concurrently with the addition of the aqueous solution, thereby carrying out the reaction.

Although the amount of (2S)-2-chloropropionic acid or methyl (2S)-2-chloropropionate is not restricted as long as it is not less than the stoichiometric amount, i.e., 1 mol equivalent of PyPOH, if it is too small, a part of PyPOH may remain unreacted and if it is too excess, the process is not economical and no prominent effect is obtained by employing such a large excess amount. Thus, the amount of (2S)-2-chloropropionic acid or methyl (2S)-2-chloropropionate may preferably be 1.05–5.0 moles per 1 mole of PyPOH.

Preferred examples of the dehydrohalogenating reagent employed in this process may include alkaline metal hydroxides and alkaline earth metal hydroxides such as lithium hydroxide, sodium hydroxide, potassium hydroxide and calcium hydroxide; alkaline metal carbonates such as lithium carbonate, sodium carbonate and potassium carbonate; and alkaline metal hydrogen carbonates such as sodium hydrogen carbonate and potassium hydrogen carbonate. Among these, in view of the economy, solubility and the like, sodium hydroxide and potassium hydroxide are preferred.

In cases where (2S)-2-chloropropionic acid is used, the requisite amount of the dehydrohalogenating reagent may be added after hydrolyzing methyl (2S)-2-chloropropionate with the equimolar dehydrohalogenating reagent. Alternatively, a prescribed amount of the dehydrohalogenating reagent required for the hydrolysis of methyl (2S)-2-chloropropionate and for the subsequent reaction may be added at a time to methyl (2S)-2-chloropropionate. Methyl (2S)-2-chloropropionate may be hydrolyzed with sodium hydroxide or potassium hydroxide. Further, the dehydrohalogenating reagent used for the reaction according to the process of the present invention may differ from that used in the hydrolysis of methyl (2S)-2-chloropropionate.

The amount of the dehydrohalogenating reagent is not restricted as long as it is not less than the total of (2S)-2-chloropropionic acid or methyl (2S)-2-chloropropionate and PyPOH in number of moles. In cases where (2S)-2-chloropropionic acid is used, the amount of the dehydrohalogenating reagent may preferably be 1.1 to 5.0 moles per one mole of the total of (2S)-2-chloropropionic acid and PyPOH, and in the other cases where (2S)-2-chloropropionic acid is used, the amount of the dehydrohalogenating reagent may preferably be 1.05 to 5.0 moles per one mole of the total of (2S)-2-chloropropionic acid methyl ester and PyPOH.

The concentration of the dehydrohalogenating reagent in the aqueous solution may preferably be in the range of 5% by weight to saturation.

The concentration of (2S)-2-chloropropionic acid in the aqueous solution is not restricted and may preferably be 2–50% by weight in order to attain easy operation.

Preferred examples of the aromatic hydrocarbon solvent used in this process may include benzene, toluene, xylene, ethylbenzene and mesitylene. Although these solvents may be used individually or in combination, it is preferred to employ a single solvent in order to attain easy treatments after the reaction.

Although the amount of the solvent is not restricted, if it is too small, it is difficult to stir the reaction mixture uniformly and to remove the water in the reation mixture completely. As the result of such operation, a yield of the reaction may be reduced. On the other hand, the use of large excess amount of the solvent does not bring about a remarkable effect and is not economy. Thus, the amount of the solvent may preferably be 5–100 times the weight of PyPOH.

In this process, the reaction may be carried out at a temperature of not lower than 40° C. and lower than 80° C. If the reaction temperature is lower than 40° C., the reaction may not proceed in some case when some kind of bases was used as dehydrohalogenating reagent, and if the reaction temperature is not lower than 80° C., both of the yield and the optical purity may be decreased.

The reaction pressure may be appropriately selected without undue experimentation according to the reaction conditions such as the solvent employed and the reaction temperature so that a stable reflux of the solution containing (2S)-2-chloropropionic acid (methyl ester) and PyPOH is attained in the above-mentioned temperature range.

In cases where (2S)-2-chloropropionic acid is used, the rate of supplying the aqueous solution containing (2S)-2-chloropropionic acid and the dehydrohalogenating reagent may preferably be not higher than the rate of dehydration by the reflux of the aromatic hydrocarbon solvent. Supplying the aqueous solution at a rate higher than the distillation rate may reduce the yield.

In cases where methyl (2S)-2-chloropropionate is used, it is preferred that the rate of adding the aqueous dehydrohalogenating reagent solution be not lower than the rate of distillation by the reflux condition. If the rate of addition of the aqueous dehydrohalogenating reagent is slower than the distillation rate, tetrahydrofurfuryl 2-(4'-(3''-chloro-5''-trifluoromethyl-2''-pyridyloxy)phenoxy) propionate becomes racemic more easily and the optical purity of the desired product may be decreased. On the other hand, if the rate of adding the aqueous dehydrohalogenating reagent is too fast, the reaction mixture may foam and the dehydration may be hindered. Thus, the rate of adding the aqueous dehydrohalogenating reagent may preferably be not slower than the rate of dehydration by azeotropic distillation, at which not more than 50% by weight of water remain in the reaction system.

The dehydration completes within one hour after the completion of the addition of the aqueous solution containing optically active (2S)-2-chloropropionic acid and the dehydrohalogenating reagent, and then the reaction is completed after 1–10 hours' aging.

The water distilled by the azeotropic distillation is removed after separation from the aromatic hydrocarbon solvent with a separator.

After completion of the reaction, the reaction mixture may be neutralized with hydrochloric acid, extracted with an organic solvent such as toluene and ether, and condensed so as to obtain the desired (2R)-2-(4'-(3''-chloro-5''-trifluoromethyl-2''-pyridyloxy)-phenoxy)propionic acid with high yield and high optical purity.

According to a sixth aspect of the present invention, a process for preparing optically active tetrahydrofurfuryl (2R)-2-(4'-(3''-chloro-5''-trifluoromethyl-2''-pyridyloxy)phenoxy propionate is provided. In this process, a solution containing (3'-chloro-5'-trifluoromethyl-2'-pyridyloxy)phenol in an aromatic hydrocarbon solvent is refluxed under reduced pressure at a temperature of not lower than 40° C. and lower than 80° C. and an alkaline aqueous solution of (2S)-2-chloropropionic acid is added to the refluxing solution so as to allow simultaneous dehydration and reaction to obtain optically active (2R)-2-(4'-(3''-chloro-5''-trifluoromethyl-2''-pyridyloxy)phenoxy)propionic acid. Without isolating and purifying the reactant, a hydrogen halide and tetrahydrofurfuryl alcohol are added to the reactant and the resulting mixture is allowed to react to obtain optically active tetrahydrofurfuryl (2R)-2-(4'-(3''-chloro-5''-trifluoromethyl-2''-pyridyloxy)phenoxy)propionate with high yield and high optical purity.

As described above, this process comprises two steps, i.e., an etherification step by the reaction between (2S)-2-chloropropionic acid and PyPOH, and an esterification step by the reaction among (2R)-2-(4'-(3''-chloro-5-trifluoro-2''-pyridyloxy)phenoxy)propionic acid (hereinafter also referred to as "PyPOPA" for short), the hydrogen halide and tetrahydrofurfuryl alcohol.

The optically active (2S)-2-chloropropionic acid may be in an acid form or a salt form.

The each step in this process will now be described in more detail.

The etherification step may be carried out in the same manner as in the process according to the fifth aspect of the present invention described above in detail wherein (2S)-2-chloropropionic acid is used as a starting material.

In the esterification step, after allowing the PyPOPA solution in the aromatic hydrocarbon solvent obtained in the etherification step to cool to room temperature, a hydrogen halide and tetrahydrofurfuryl alcohol are added to the reaction mixture without isolating or purifying the reaction product in the etherification step, and the resulting mixture is allowed to react so as to obtain the desired optically active propionate derivative.

Preferred examples of the hydrogen halide used in this process may include hydrogen fluoride, hydrogen chloride, hydrogen bromide and hydrogen iodide. Among these, in view of the reactivity and ease of handling, hydrogen chloride and hydrogen bromide are preferred.

Although the amount of the hydrogen halide is not restricted, it if is too excess, the reaction operation may be troublesome and if it is too small, it takes a long time to complete the reaction. Thus, the amount of the hydrogen halide may preferably be 0.01–0.20 part by weight with respect to one part by weight of tetrahydrofurfuryl alcohol.

The amount of tetrahydrofurfuryl alcohol is not restricted as long as it is not less than the stoichiometric amount, i.e., one mole per one mole of PyPOPA, if it is too small, it takes a long time to complete the reaction and if it is too excess, the process is not economical. Thus, from the practical point of view, the amount of tetrahydrofurfuryl alcohol may preferably be 5–100 moles per one mole of PyPOPA.

The esterification reaction may be carried out at a temperature of 5°–150° C. lower than the boiling point of the solvent employed. Since the reaction rate of this reaction is larger than the other esterification reactions, the reaction may be well carried out usually at a temperature of 5°–80° C.

Although the time required for completing the reaction varies depending on the ratio of the starting materials and on the reaction temperature, usually 0.5 to 50 hours is sufficient for completing the reaction.

By distilling the reaction product so as to remove the solvent, hydrogen halide and excess tetrahydrofurfuryl alcohol, the optically active propionate derivative of the formula [III] may also be obtained.

The invention will now be described by way of examples thereof. The examples are presented for the illustration purpose only and should not be interpreted in any restrictive way.

In the following examples, the optical purity was determined by high performance liquid chromatography using a racemate separation column Chiral Cell OK commercially available from Daicel Chemical Industries, Ltd.

EXAMPLE 1

To a solution containing 18.1 g of potassium carbonate in 350 ml of acetonitrile, 34.5 g of (2R)-2-(4-hydroxyphenoxy)propionic acid tetrahydrofurfuryl ester (optical purity of 99%) and 25.6 g of 2,6-dichloroquinoxaline were added and the resulting mixture was heated to reflux overnight under stirring. After allowing the mixture to cool to room temperature, the solids in the reaction mixture were removed by filtration and the solids on the filter paper were washed twice with 100 ml each of acetonitrile. The filtrate was evaporated under reduced pressure and the residue was purified by silica gel column chromatography (eluant: hexane) and obtained 34.3 g of the desired product. The optical purity of the thus obtained product with (2R)-configuration was 96.5%.

EXAMPLE 2

The same procedure as used in Example 1 was repeated except that the reactants were 14.0 g of potassium carbonate, 25.1 g of tetrahydrofurfuryl (2R)-2-(4-hydroxyphenoxy)propionate (optical purity of 98%) and 18 g of 2-chloro-5-trifluoromethylpyridine, obtained 28.3 g of the desired product. The optical purity of the thus obtained product with (2R)-configuration was 93%.

EXAMPLE 3

The same procedure as in Example 2 was repeated except that 21.5 g of 2,3-dichloro-5-trifluoromethylpyridine was used in place of 2-chloro-5-trifluoromethylpyridine and obtained 29.3 g of the desired product. The optical purity of the thus obtained product with (2R)-configuration was 95%.

EXAMPLE 4

The same procedure as in Example 3 was repeated except that 5 g of sodium hydroxide was used in place of the potassium carbonate and obtained 15.4 g of the desired product. The optical purity of the thus obtained product with 2R-configuration was 85.4%.

EXAMPLE 5

The same procedure as in Example 1 was repeated except that 18.3 g of 2,3,5-trichloropyridine and 25.0 g of tetrahydrofurfuryl (2R)-2-(4-hydroxyphenoxy)propionate (optical purity of 99%) were used in place of 2,6-dichloroquinoxaline and (2R)-2-(4-hydroxyphenoxy)propionic acid tetrahydrofurfuryl ester, respectively and obtained 27.3 g of the desired product. The optical purity of the thus obtained product with 2R-configuration was 97.3%.

REFERENCE EXAMPLE 1

In a 500 ml three-necked flask, 15.0 g of potassium carbonate, 21.0 g of 4-(3'-chloro-5'-trifluoromethyl-2'-pyridyloxy)phenol and 300 ml of N,N-dimethylsulfoxide were placed and the resulting mixture was stirred at room temperature. To this mixture, 150 g of (2S)-methyl 2-chloropropionate was dropped for 1 hour under stirring and the resulting mixture was allowed to react for another 5 hours.

The resulting mixture was poured into 1 liter of 3N hydrochloric acid and the resultant was extracted three times with 200 ml each of chloroform. The extract was dried, condensed and filtered with silica gel to obtain 25.9 g of methyl (2R)-2-(4'-(3"-chloro-5"-trifluoro-2"-pyridyloxy)phenoxy)propionate. The optical purity of the thus obtained product with (2R)-configuration was 98% e.e. and the specific rotation $[\alpha]_D^{20} = +36.2$ (CHCl$_3$).

REFERENCE EXAMPLE 2

The same procedure as in Reference Example 1 was repeated except that 9.5 g of hydroquinone was used in place of 4-(3'-chloro-5'-trifluoromethyl-2'-pyridyloxy)phenol and obtained 14.3 g of methyl (2R)-2-(4'-hydroxyphenoxy)propionate. The optical purity of the thus obtained product with (2R)-configuration was 97% e.e. and the specific rotation $[\alpha]_D^{20}$ was +27.5 (CHCl$_3$).

EXAMPLE 6

In a 500 ml three-necked flask with Liebig condenser, 25.2 g of methyl (2R)-2-(4'-(3"-chloro-5"-trifluoromethyl-2"-pyridyloxy)phenoxy)propionate, 15.8 g of tetrahydrofurfuryl alcohol (hereinafter also referred to as "THFA"), 69.3 mg of p-toluenesulfonic acid and 260 ml of benzene were placed, and the mixture was heated to reflux at 80° C. for 5.0 hours so as to allow the mixture to react.

After completion of the reaction, the mixture was allowed to cool and was washed with 1% aqueous sodium hydrogen carbonate, followed by drying and condensation, 28.4 g of the desired tetrahydrofurfuryl (2R)-2-(4'-(3"-chloro-5"-pyridyloxy)phenoxy)propionate was obtained.

Analysis:
$n_D^{25} = 1.5618$.
$[\alpha]_D^{20} = +33.6$ (CHCl$_3$).
Optical Purity: 98% e.e.

EXAMPLES 7-9

The same procedure as in Example 6 was repeated except that the reaction conditions were as indicated in Table 1 below and (2R)-methyl 2-(4'-(3"-chloro-5"-trifluoromethyl-2"-pyridyloxy)phenoxy propionate obtained in the above-described Reference Example 1 or (2R)-methyl 2-(4'-hydroxyphenoxy)propionate obtained in the above-described Reference Example 2 was employed. The results of the analysis are also shown in Table 1.

TABLE 1

| R | THFA | Catalyst | | Solvent | |
|---|---|---|---|---|---|
| g (mmol) | g (mmol) | Name | Amount Used mg (mmol) | Name | Amount Used ml |

TABLE 1-continued

| | | | | | | | |
|---|---|---|---|---|---|---|---|
| Example 6 | 3-chloro-5-triflurormethyl-2-pyridyl 25.2 (67.1) | 15.8 (154.7) | p-Toluenesulfonic Acid | 69.3 (0.402) | Benzene | 260 | |
| Example 7 | 3-chloro-5-trifluoromethyl-2-pyridyl 8.0 (21.1) | 17.2 (168.4) | Sulfuric Acid | 1.5 (0.015) | Ethylbenzene | 300 | |
| Example 8 | 3-chloro-5-trifluoromethyl (10.6) | 18.4 (180.2) | Trifluoroacetic Acid | 84.6 (0.742) | Dichloromethane | 380 | |
| Example 9 | Hydrogen 20.1 (102.4) | 200 (1958.3) | Methanesulfonic Acid | 295.2 (3.072) | — | — | |

| | Reaction Conditions | | | | |
|---|---|---|---|---|---|
| | Temperature (°C.) | Time (hrs) | Yield (%) | Conversion Ratio (%) | Analysis Value |
| Example 6 | 80 | 5.0 | 95 | 98 | $n_D^{25} = 1.5618$<br>$[\alpha]_D^{20} = +33.6$<br>Optical Purity 98% e.e. |
| Example 7 | 120 | 2.0 | 93 | 99 | $n_D^{25} = 1.5622$<br>$[\alpha]_D^{20} = +33.5$<br>Optical Purity 98% e.e. |
| Example 8 | 40 | 48.0 | 98 | 99 | $n_D^{25} = 1.5625$<br>$[\alpha]_D^{20} = +33.3$<br>Optical Purity 98% e.e. |
| Example 9 | 145 | 14.0 | 94 | 95 | $n_D^{25} = 1.5414$<br>$[\alpha]_D^{20} = +25.0$<br>Optical Purity 94% e.e |

EXAMPLE 10

In a 500 ml three-necked flask equipped with a stirrer, 280 g of THFA was placed and anhydrous hydrogen chloride was bubbled therein for 60 minutes at a flow rate of 35 ml/min.

After the hydrogen chloride was absorbed, the total weight of the reaction apparatus was measured. As a result, it was determined that 3.0 g of hydrogen chloride was dissolved in THFA.

Then 10.0 g of (2R)-2-(4'-(3''-chloro-5''-trifluoromethyl-2''-pyridyloxy)phenoxy)propionic acid (optical purity of 97% e.e.) prepared by a conventional procedure was added to the mixture and the resulting mixture was stirred at 20° C. for 4 hours.

Excess THFA was removed from the reaction mixture under reduced pressure and 100 ml of ether was added to the resultant. The resulting mixture was then washed with 50 ml of saturated aqueous sodium hydrogen carbonate, the organic phase was dried over anhydrous magnesium sulfate, condensed and obtained 11.7 g of the desired product tetrahydrofurfuryl (2R)-2-(4'-3''-chloro-5''-trfluoromethyl-2''-pyridyloxy)phenoxy) propionate. The change in the optical purity was not observed between before and after the reaction.

EXAMPLES 11 AND 13

The same procedure as in Example 10 was repeated except that the reaction conditions were as shown in Table 2 below and (2R)-2-(4'-hydroxyphenoxy)propionic acid (optical purity of 95% e.e.) was used in place of (2R)-2-(4'-(3''-chloro-5''-trifluoromethyl-2''-pyridyloxy)phenoxy)propionic acid. The results of the analysis are also shown in Table 2.

EXAMPLES 12 AND 14

The same procedure as in Example 10 was repeated except that the reaction conditions were as shown in Table 2 below. The results of the analysis are also shown in Table 2.

TABLE 2

| | R | | THFA g (mmol) | Hydrogen Halide g | Solvent | |
|---|---|---|---|---|---|---|
| | g | (mmol) | | | Name | Amount Used (ml) |
| Example 10 | 3-chloro-5-trifluoromethyl-2-pyridyl 10.0 | (27.65) | 280 (2741.60) | HCl 3.0 | — | — |
| Example 11 | Hydrogen 30.0 | (164.67) | 120 (1174.97) | HCl 15.0 | — | — |
| Example 12 | 3-chloro-5-trifluoromethyl-2-pyridyl 10.0 | (27.65) | 42 (411.24) | HBr 4.5 | Benzene | 280 |
| Example 13 | Hydrogen 15.0 | (82.34) | 252 (2467.44) | HBr 38.0 | Xylene | 200 |
| Example 14 | 3-chloro-5-trifluoromethyl-2-pyridyl 50.0 | (138.24) | 71 (695.19) | HCl 8.0 | Carbon Tetrachloride | 150 |

| | Reaction Conditions | | | | |
|---|---|---|---|---|---|
| | Temperature (°C.) | Time (hrs) | Yield (%) | Conversion (%) | Analysis Value |

TABLE 2-continued

| | | | | | |
|---|---|---|---|---|---|
| Example 10 | 20 | 4.0 | 95 | 100 | $n_D^{25} = 1.5619$ |
| | | | | | $[\alpha]_D^{20} = +33.2$ |
| | | | | | Optical Purity 97% ee |
| Example 11 | 50 | 8.0 | 92 | 98 | $n_D^{25} = 1.5413$ |
| | | | | | $[\alpha]_D^{20} = +25.3$ |
| | | | | | Optical Purity 95% ee |
| Example 12 | 40 | 0.5 | 96 | 99 | $n_D^{25} = 1.5620$ |
| | | | | | $[\alpha]_D^{20} = +33.1$ |
| | | | | | Optical Purity 97% ee |
| Example 13 | 80 | 1.0 | 95 | 97 | $n_D^{25} = 1.5415$ |
| | | | | | $[\alpha]_D^{20} = +25.2$ |
| | | | | | Optical Purity 95% ee |
| Example 14 | 50 | 2.0 | 94 | 100 | $n_D^{25} = 1.5621$ |
| | | | | | $[\alpha]_D^{20} = +33.2$ |
| | | | | | Optical Purity 97% ee |

REFERENCE EXAMPLE 3

In a 2000 ml three-necked round flask equipped with a water separator, Liebig condenser and a stirrer, 200 g of D-lactic acid, 350 ml of benzene and 4.0 g of sulfuric acid were placed and the mixture was dehydrated for 6 hours by heating to reflux.

After the dehydration, the mixture was cooled and 890 g of THFA was added to the mixture. The mixture was again heated to reflux so as to allow the reaction.

After neutralizing the resulting mixture with aqueous sodium acetate, the solvent was removed and the residue was distilled under reduced pressure and obtained 285 g of the desired tetrahydrofurfuryl (2R)-lactate.

Analysis:
Boiling Point: 96°-97° C./2 mm Hg.
Specific Rotation $[\alpha]_D^{20} = +11.92$ (CHCl$_3$, 0.1).

REFERENCE EXAMPLE 4

In a 500 ml three-necked round flask equipped with a 100 ml dropping funnel and a stirrer, 59 g of thionyl chloride and 100 ml of dichloromethane were placed. While dipping the flask in a water bath, 50 g of tetrahydrofurfuryl (2R)-lactate was dropped for one hour using a dropping funnel at a temperature of 15°-35° C.

The reaction mixture was stirred under reduced pressure at room temperature so as to remove the hydrogen chloride generated as a byproduct, excess thionyl chloride and dichloromethane to obtain crude tetrahydrofurfuryl (2R)-2-chlorosulfuroxy propionate.

The subsequent steps were carried out without purifying the thus obtained crude (2R)-tetrahydrofurfuryl 2-chlorosulfuroxy propionate.

In a 300 ml three-necked flask equipped with a Dimroth condenser, 300 ml distillation receiving vessel connected with pressure-reduction line with an acidic gas trap, 150 ml of liquid paraffin and 1.0 ml of hexamethylenephosphortriamide were placed. On the other hand, 80 g of the crude tetrahydrofurfuryl (2R)-2-chlorosulfuroxy propionate obtained above was fed. The flask was heated to an internal temperature of 130° C. in an oil bath while reducing the pressure inside the flask to 0.5 mmHg.

Under these conditions, tetrahydrofurfuryl (2R)-2-chlorosulfuroxy propionate was dropped from the dropping funnel so as to decompose the same simultaneously with the dropping to distill out the desired tetrahydrofurfuryl (2S)-2-chloropropionate. The dropping was conducted over 3 hours to obtain 58.3 g of distillate.

Analysis:
Specific Rotation $[\alpha]_D^{20} = -8.52$ (acetone, 0.1).
Optical Purity: 97.2% e.e.

EXAMPLE 15

In a 500 ml three-necked round flask equipped with a stirrer, 100 ml of anhydrous N,N-dimethylsulfoxide, 21.9 g of potassium carbonate and 10.0 g of hydroquinone were placed and the mixture was stirred. To this mixture, 21.9 g of the tetrahydrofurfuryl (2S)-2-chloropropionate was dropped from the dropping funnel over 30 minutes. After the completion of the addition, the reaction mixture was allowed to react for another 3 hours.

After completion of the reaction, dimethylsulfoxide was removed under reduced pressure at 40° C. and 500 ml of 1N hydrochloric acid was added thereto. The resulting mixture was extracted three times with 100 ml each of chloroform and the resultant was dried over anhydrous magnesium sulfate, condensed and filtered with silica gel to obtain 20.9 g of the desired tetrahydrofurfuryl (2R)-2-(4'-hydroxyphenoxy)propionate.

Analysis:
$n_D^{25} = 1.5126$.
Specific Rotation $[\alpha]_D^{20} = 27.0$ (CHCl$_3$, 0.1).
Optical Purity: 82% e.e.

EXAMPLES 16–18

The same procedure as in Example 15 was repeated except that the reaction conditions were as shown in Table 3 below. The results of analysis of the obtained products are also shown in Table 3.

TABLE 3

| | R | Dehydrohalognating Reagent | Tetrahydrofurfuryl (2S)-2-chloropropionate | Solvent | |
|---|---|---|---|---|---|
| | g (mmol) | g (mmol) | g (mol) | Kind of Solvent | Volume (ml) |
| Example 15 | hydrogen atom 10.0 (90.8) | potassium carbonate 6.9 (49.9) | 21.9 (113.7) | N,N-dimethylsulfoxide | 100 |
| Example 16 | 3-chloro-5-trifluoromethyl-2- | sodium carbonate 7.8 | 16.9 (87.7) | N-methylpyrrolidolidone | 150 |

TABLE 3-continued

| | | | | | | |
|---|---|---|---|---|---|---|
| | pyridyl 8.5 (29.3) | (73.6) | | | | |
| Example 17 | hydrogen atom 6.5 (59.0) | sodium carbonate 9.4 (88.7) | 90.9 (471.9) | | methylethyl- ketone | 180 |
| Exampel 18 | 3-chloro-5- trifluoro- methyl-2- Pyridyl 16.0 (55.2) | potassium carbonate 38.1 (275.7) | 180.0 (934.4) | | dimethyl- formamide | 80 |

| | Reaction Conditions | | | Conversion | |
|---|---|---|---|---|---|
| | Temperature (°C.) | Time (hrs) | Yield (%) | Ratio (%) | Analytical Value |
| Example 15 | 30 | 2.0 | 92 | 100 | $n_D^{25} = 1.5126$ $[\alpha]_D^{20} = +27.0$ optical purity: 82% e.e. |
| Example 16 | 70 | 8.0 | 79 | 98 | $n_D^{25} = 1.5602$ $[\alpha]_D^{20} = +29.5$ optical purity: 88% e.e. |
| Example 17 | 60 | 36.0 | 89 | 99 | $n_D^{25} = 1.5135$ $[\alpha]_D^{20} = +30.1$ optical purity: 92% e.e. |
| Example 18 | 20 | 24.0 | 85 | 97 | $n_D^{25} = 1.5634$ $[\alpha]_D^{20} = +28.5$ optical purity: 85% e.e. |

EXAMPLE 19

In a 300 ml three-necked round flask equipped with a stirrer, water separator with Liebig condenser and a 50 ml dropping funnel, 10.20 g of 4-(3'-chloro-5'-trifluoromethyl-2'-pyridyloxy)phenol and 100 ml of toluene were placed and the mixture was stirred. 27.35 g of Aqueous solution prepared from 4.57 g of methyl (2S)-2-chloropropionate and 4.35 g of sodium hydroxide was placed in the dropping funnel. This system was connected to a pressure-reducing line so as to reduce the pressure in the flask to 170 mmHg. Upon heating the flask in an oil bath, the reflux started at an internal temperature of 75° C.

Then the aqueous sodium hydroxide solution containing (2S)-2-chloropropionic acid was dropped from the dropping funnel over 1.5 hours and the dehydration was carried out by distillation simultaneously with the dropping so as to proceed the reaction. After completion of the dropping, the mixture was allowed to stand heating another 1.5 hours. The internal temperature during the dropping was 72° C. and that during the aging was 75° C. It was observed that the distilling out of water ended about 10 minutes after the completion of the addition.

After cooling the reaction mixture, 50 ml of 10% hydrochloric acid was added thereto and the resultant was separated. The aqueous layer was extracted three times with 20 ml each of toluene. The organic layer was dried over magnesium sulfate and condensed to obtain 12.3 g of crude (2R)-2-(4'-(3''-chloro-5''-trifluoromethyl-2''-pyridyloxy)phenoxy)propionic acid.

Reverse phase high performance liquid chromatography of the product revealed that the purity (including the racemic compound) was 94.2% (yield in terms of pure product of 11.59 g; yield based on 4-(3'-chloro-5'-trifluoromethyl-2'-pyridyloxy)phenol of 91%), and the optical purity was 92% e.e.

EXAMPLES 20-23

The same procedure as in Example 19 was repeated except that the reaction conditions were as shown in Table 4 below, and that a 2-liter three-necked round flask was used in Example 20 and a 500 ml of three-necked round flask was used in Examples 21 and 23. The results of the analysis of the products are also shown in Table 4.

COMPARATIVE EXAMPLE 1

The same procedure as in Example 19 was repeated except that the reaction conditions were as shown in Table 4 and the dehydration was carried out by reflux with toluene at atmospheric pressure. The results of the analysis are shown in Table 4.

COMPARATIVE EXAMPLE 2

The same procedure as in Example 20 was repeated except that the reaction conditions were as shown in Table 4 and the reaction was carried out without dehydration. The results of the analysis are shown in Table 4.

COMPARATIVE EXAMPLE 3

The same procedure as in Example 19 was repeated except that the reaction conditions were as shown in Table 4 and the reaction was carried out without dehydration. The results of the analysis are shown in Table 4.

COMPARATIVE EXAMPLE 4

Using the same reaction apparatus as in Example 19, 18 g of 4-(3'-chloro-5'-trifluoromethyl-2'-pyridyloxy)-phenol was dissolved in 100 ml of toluene and the mixture was heated to 60° C. To the resulting mixture, 7.0 g of sodium hydroxide was added and the resultant was stirred for 30 minutes at 70° C. To the resulting mixture, was added 8.8 g of (2S)-2-chloropropionic acid prepared from (2S)-2-chloropropionic acid methyl ester (The (2S)-2-chloropropionic acid methyl ester was prepared by hydrolyzing (2S)-2-chloropropionic acid methyl ester with equimolar 20% aqueous sodium hydroxide solution and neutralizing the resultant, followed by extraction with ether and condensation).

After stirring the mixture at the same temperature for another one hour, 7.6 g of sodium hydroxide was added thereto and the resulting mixture was heated to 110° C. so as to allow the mixture to react for 1.5 hours under reflux.

The resulting mixture was cooled and process in the same manner as in Example 19 to obtain 17.5 g of an oil.

The product was analyzed as in Example 19. The purity was 85%, yield 67%, conversion rate 100% and optical purity 56% e.e.

observed that most of water was obtained within 30 minutes after end of addition.

The conversion of PyPOH determined by reverse phase high performance liquid chromatography was 100%.

TABLE 4

| | PyPOH[1] g (mmol) | CPA[2] g (mmol) | Dehydrohalogenating Reagent Name | Weight g (mmol) | Water g | Solvent Name | weight g | Dropping Time of Aqueous Solution of CPA (hrs) |
|---|---|---|---|---|---|---|---|---|
| Example 19 | 10.20 (35.22) | 4.05 (37.32) | sodium hydroxide | 4.35 (108.8) | 23 | toluene | 100 | 1.5 |
| Example 20 | 15.61 (53.89) | 11.69 (107.72) | sodium hydroxide | 7.63 (190.8) | 94 | benzene | 1400 | 11.0 |
| Example 21 | 12.25 (42.29) | 22.12 (203.83) | potassium hydroxide | 27.64 (492.6) | 220 | xylene | 70 | 1.0 |
| Example 22 | 18.43 (63.63) | 10.34 (95.28) | potassium hydroxide[3] | 40.10 (714.7) | 60 | toluene | 400 | 3.5 |
| Example 23 | 20.21 (69.77) | 9.84 (90.67) | sodium hydroxide[3] | 20.53 (513.3) | 240 | ethyl-benzene | 105 | 2.0 |
| Comparative Example 1[4] | 12.61 (43.53) | 5.10 (47.00) | potassium hydroxide | 5.86 (104.4) | 26 | toluene | 120 | 2.0 |
| Comparative Example 2[5] | 18.50 (63.87) | 7.28 (67.08) | sodium hydroxide | 8.90 (222.5) | 70 | benzene | 1000 | 7.0 |
| Comparative Example 3[5] | 10.20 (35.22) | 16.49 (37.32) | sodium hydroxide | 4.35 (108.8) | 23 | toluene | 100 | 1.5 |

| | Reaction Temperature (°C.) | Aging Temperature (°C.) | Aging Time (hrs) | Pressure (mmHg) | Yield (%) (containing optical isomer) | Conversion Ratio (%) | Analytical Value |
|---|---|---|---|---|---|---|---|
| Example 19 | 72 | 75 | 1.5 | 170 | 91 | 100 | optical purity: 92% e.e. |
| Example 20 | 59 | 62 | 2.5 | 400 | 86 | 99 | optical purity: 95% e.e. |
| Example 21 | 42 | 43 | 6.0 | 18 | 93 | 98 | optical purity: 97% e.e. |
| Example 22 | 76 | 78 | 1.0 | 190 | 90 | 100 | optical purity: 90% e.e. |
| Example 23 | 52 | 55 | 4.5 | 30 | 88 | 99 | optical purity: 93% e.e. |
| Comparative Example 1[4] | 110 | 110 | 1.5 | 760 | 72 | 100 | optical purity: 62% e.e. |
| Comparative Example 2[5] | 30 | 30 | 9.0 | 760 | 35 | 46 | optical purity: 88% e.e. |
| Comparative Example 3[5] | 73 | 73 | 1.5 | 760 | 46 | 52 | optical purity: 90% e.e. |

[1]PyPOH: 4-(3'-chloro-5'-trifluoromethyl-2'-pyridyloxy)phenol
[2]CPA: (2S)-2-chloropropionic acid, The values in parentheses mean theoretical values of the product prepared by hydrolysis.
[3]In Examples 22 and 23, after methyl (2S)-2-chloropropionate was hydrolyzed, excess dehydrohalogenating reagent was then further added thereto.
[4]The dehydration was conducted under atmospheric pressure by reflux with toluene.
[5]The reaction was conducted under atmospheric pressure without dehydration.

EXAMPLE 24

In a 300 ml three-necked round flask equipped with a stirrer, water separator with Liebig condenser and a 50 ml dropping funnel, 15.61 g of 4-(3'-chloro-5'-trifluoromethyl-2'-pyridyloxy)phenol and 150 ml of toluene were placed and the mixture was stirred. Aqueous solution prepared from 9.91 g of (2S)-2-chloropropionic acid methyl ester and 23.82 g of aqueous sodium hydroxide solution containing 5.82 g of sodium hydroxide was placed in the dropping funnel. The upper end of the Liebig condenser was conncected to a vacuum line and the pressure of the inside of the flask was reduced to 90 mmHg. The flask was heated in an oil bath and the reflux started at an internal temperature of 55° C.

Then the aqueous sodium hydroxide solution was added from the dropping funnel over 0.5 hours, and the dehydration was carried out simultaneously with the dropping by the reflux so as to allow the mixture to react. After completion of the dropping, the resulting reaction mixture was aged for another 5.0 hours. The internal temperature of the flask during the dropping was 55° C. and that during the aging was 60° C. It was The reaction mixture was cooled and 16.51 g of THFA was added thereto. In the resulting solution, hydrogen chloride gas was bubbled for 60 minutes at a rate of 35 ml/min.

After the hydrogen chloride was absorbed, the overall weight of the reaction apparatus was measured. As a result, it was determined that the amount of the dissolved hydrogen chloride was 6.0 g.

The resulting mixture was allowed to stand at 40° C. for 6 hours under stirring. After removing the excess THFA under reduced pressure, 100 ml of ether was added to the mixture and the resultant was washed with 50 ml of saturated aqueous sodium hydrogen carbonate. The organic layer was dried and condensed to obtain 20.40 g of the desired tetrahydrofurfuryl (2R)-2-(4'-(3''-chloro-5''-trifluoromethyl-2''-pyridyloxy)phenoxy)propionate. The optical purity of the product was 98% e.e.

EXAMPLES 25-27

The same procedure as in Example 24 was repeated except that the reaction conditions were as shown in Table 5 below, and that a 500 ml three-necked round flask was used in Examples 25 and 26, and a 1-liter three-necked round flask was used in Example 27. The results of the analysis are shown in Table 5.

| Etherification Step | Example 24 | Example 25 | Example 26 | Example 27 |
|---|---|---|---|---|
| PyPOH[1] g (mmol) | 15.61 (53.89) | 20.21 (69.77) | 12.25 (42.29) | 18.43 (63.63) |
| CPA[2] g (mmol) | 8.77 (80.84) | 15.15 (139.5) | 22.12 (203.8) | 9.32 (85.90) |
| Dehydrohalogenating | sodium hydroxide | sodium hydroxide | potassium hydroxide | potassium hydroxide |
| Reagent g (mmol) | 5.82 (145.5) | 9.77 (244.2) | 27.64 (492.6) | 10.71 (190.9) |
| Water g | 18 | 30 | 220 | 50 |
| Solvent g | toluene 150 | benzene 200 | xylene 70 | toluene 400 |
| Dropping Time of Aqueous Solution of CPA[2] (hrs) | 0.5 | 2.0 | 1.0 | 3.5 |
| Reaction Temperature (°C.) | 55 | 59 | 42 | 76 |
| Aging Temperature (°C.) | 60 | 62 | 43 | 78 |
| Aging Time (hrs) | 5.0 | 8.0 | 6.0 | 2.0 |
| Pressure (mmHg) | 90 | 400 | 18 | 190 |
| Conversion[3] (%) | 100 | 99 | 98 | 98 |
| THFA[4] g (mmol) | 16.51 (161.7) | 35.63 (348.9) | 43.19 (422.9) | 130.2 (1272) |
| Hydrogen Halide | hydrogen chloride | hydrogen chloride | hydrogen chloride | hydrogen bromide |
| g | 6.0 | 12.7 | 18.25 | 30 |
| Reaction Temperature (°C.) | 40 | 50 | 30 | 60 |
| Reaction Time (hrs) | 6.0 | 8.0 | 4.0 | 5.0 |
| Yield[5] (%) | 94 | 93 | 90 | 92 |
| Conversion Ratio[6] (%) | 99 | 97 | 95 | 96 |
| Analytical Value | $n_D^{25} = 1.5622$ | $n_D^{25} = 1.5518$ | $n_D^{25} = 1.5428$ | $n_D^{25} = 1.5648$ |
| | $[\alpha]_D^{20} = +33.5$ | $[\alpha]_D^{20} = +33.2$ | $[\alpha]_D^{20} = +32.5$ | $[\alpha]_D^{20} = +33.4$ |
| | optical purity: 98% e.e | optical purity: 97% e.e | optical purity: 95% e.e | optical purity: 98% e.e |

[1] PyPOH: 4-(3'-chloro-5'-trifluoromethyl-2'-pyridyloxy)phenol
[2] CPA: (2S)-2-chloropropionic acid, The values in parentheses mean theoretical values of the product prepared by hydrolysis.
[3] Conversion of PyPOH
[4] THFA: tetrahydrofulfurylalcohol
[5] Yield was calculated based on PyPOH
[6] Conversion of PyPOPA ((2S)-2-(4'-(3''-chloro-5''-trifluoromethyl-2''-pyridyloxy)phenoxy)propionic acid).

EXAMPLE 28

In a 300 ml three-necked round flask equipped with a stirrer, water separator with Liebig condenser and a 50 ml dropping funnel, 9.2 g of methyl (2S)-2-chloropropionate, 20.5 g of 4-(3'-chloro-5'-trifluoromethyl-2'-pyridyloxy)phenol and 115 ml of toluene were placed and the mixture was stirred so as to dissolve the solids.

Then an aqueous solution containing 6.3 g of sodium hydroxide in 7.7 g of water was placed in the dropping funnel and the upper end of the Liebig condenser was connected to a pressure-reducing line so as to reduce the pressure in the flask to 200 mmHg. The flask was heated in an oil bath and a stable reflux was attained at an internal temperature of 63° C.

To this mixture, the aqueous sodium hydroxide was added dropwise over 1.5 hours and the mixture was aged under the same pressure for additional 4 hours. The temperature of the reaction mixture during thd dropping was 60° C. and that during the aging was 63° C. The rate of dehydration by the reflux during the dropping of the sodium hydroxide solution was 3.6 ml/hr.

After cooling the obtained reaction mixture, 100 ml of 5N hydrochloric acid was added thereto and the resultant was extracted three times with 50 ml each of toluene. The extract was dried over magnesium sulfate and condensed to obtain 24.3 g of light yellow oil.

Analysis by reverse phase high performance liquid chromatography revealed that the purity was 91.8%, the yield of the desired (2R)-2-(4'-(3''-chloro-5''-trifluromethyl-2''-pyridyloxy)phenoxy)propionic acid was 22.3 g (yield based on the 4-(3'-chloro-5'-trifluoromethyl-2'-pyridyloxy)phenol was 87%), and starting material 4-(3'-chloro-5'-trifluoromethyl-2'-pyridyloxy)phenol was under the detection limit. The optical purity was 92% e.e.

EXAMPLES 29-32

The same procedure as in Example 28 was repeated except that the reactin conditions were as shown in Table 6 below and that a 2000 ml three-necked round flask was used in Examples 29, 30 and 32. The results of the analysis of the products are also shown in Table 6.

COMPARATIVE EXAMPLES 5 AND 6

The same procedure as in Example 28 was repeated except that the reaction conditions were as shown in Table 6 below and that the dehydration was conducted by reflux with toluene under atmospheric pressure in Comparative Example 5 and the dehydration was not conducted in Comparative Example 6. The results of the analysis of the products are also shown in Table 6.

TABLE 6

| | PyPOH[1] g (mmol) | CPA[2] g (mmol) | Dehydrohalogenating Reagent | | | Water g | Solvent | | Dropping Time of Aqueous Solution of Dehydrohalogenating Reagent (hrs) |
|---|---|---|---|---|---|---|---|---|---|
| | | | Name | Weight g (mmol) | | | Name | weight g | |
| Example 28 | 20.5 (70.8) | 9.2 (75.1) | sodium hydroxide | 6.3 (157.5) | | 7.7 | toluene | 115 | 1.5 |
| Example 29 | 21.8 (75.3) | 18.5 (151.0) | potassium hydroxide | 38.1 (679.0) | | 70.8 | benzene | 1000 | 3.0 |
| Example 30 | 10.6 (38.6) | 21.5 (175.4) | sodium hydroxide | 40.7 (1017.5) | | 44.1 | xylene | 1000 | 4.5 |
| Example 31 | 18.2 (62.8) | 23.1 (188.5) | potassium hydroxide | 35.3 (629.1) | | 141 | ethylbenzene | 120 | 0.5 |
| Example 32 | 15.6 (53.9) | 16.5 (134.6) | sodium hydroxide | 15.1 (377.5) | | 200 | mesitylene | 1000 | 8.0 |

TABLE 6-continued

| | | | | | | | | |
|---|---|---|---|---|---|---|---|---|
| Comparative Example 5[3] | 20.4 (70.4) | 9.3 (75.9) | sodium hydroxide | | 6.5 (162.5) | 8.0 | toluene | 120 | 1.5 |
| Comparative Example 6[4] | 20.3 (70.0) | 9.3 (75.9) | potassium hydroxide | | 38.3 (682.6) | 70.0 | benzene | 200 | 3.0 |

| | Reaction Temperature (°C.) | Aging Temperature (°C.) | Aging Time (hrs) | Dehydration Rate (ml/hrs) | Pressure (mmHg) | Yield (%) (containing optical isomer) | Conversion Ratio (%) | Analytical Value |
|---|---|---|---|---|---|---|---|---|
| Example 19 | 60 | 63 | 4.0 | 3.6 | 200 | 87 | 100 | optical purity: 92% e.e |
| Example 20 | 42 | 43 | 6.0 | 10.0 | 250 | 92 | 98 | optical purity: 95% e.e. |
| Example 21 | 50 | 52 | 8.0 | 15.0 | 30 | 91 | 99 | optical purity: 95% e.e. |
| Example 22 | 70 | 75 | 20.0 | 12.0 | 100 | 87 | 100 | optical purity: 91% e.e. |
| Example 23 | 60 | 63 | 3.0 | 22.0 | 25 | 89 | 99 | optical purity: 93% e.e. |
| Comparative Example 5[3] | 111 | 112 | 4.0 | 3.7 | 760 | 88 | 100 | optical purity: 60% e.e. |
| Comparative Example 6[4] | 60 | 60 | 6.0 | — | 760 | 52 | 100 | optical purity: 89% e.e. |

[1] PyPOH: 4-(3'-chloro-5'-trifluoromethyl-2'-pyridyloxy)phenol
[2] CPA: (2S)-2-chloropropionic acid, The value in parentheses means a theoretical value of the product.
[3] The dehydration was conducted under atmospheric pressure by reflux with toluene.
[4] The reaction was conducted under atmospheric pressure without dehydration.

We claim:

1. A process of producing (2R)-2-(4'-(3''-chloro-5''-trifluoromethyl-2''-pyridyloxy)phenoxy)propionic acid consisting essentially of the steps of:

refluxing a solution containing methyl (2S)-2-chloropropionate and 4-(3'-chloro-5'-trifluoromethyl-2'-pyridyloxy)phenol) in an aromatic hydrocarbon solvent at a temperature of not lower than 40° C. and lower than 80° C. under reduced pressure; and adding thereto an aqueous solution of a dehydrohalogenating reagent while continuing the reflux so as to hehydrate the resulting mixture concurrently with the addition of said aqueous solution, thereby carrying out the reaction.

* * * * *